US009513267B1

(12) United States Patent
Dolgov et al.

(10) Patent No.: US 9,513,267 B1
(45) Date of Patent: Dec. 6, 2016

(54) REACTOR FOR NEAR ABSOLUTE CONVERSION OF ALTERNATIVE MOIETY-CONTAINING SPECIES INTO A SELECT MOIETY-CONTAINING SPECIES AND ANALYTICAL INSTRUMENT EMPLOYING THE REACTOR

(71) Applicant: Mocon, Inc., Minneapolis, MN (US)

(72) Inventors: Boris Dolgov, Broomfield, CO (US);
Brian G. Bischof, Mead, CO (US);
Stephen A. Grantham, Johnstown, CO (US)

(73) Assignee: Mocon, Inc., Minneapolis, MN (US)

( * ) Notice: Subject to any disclaimer, the term of this patent is extended or adjusted under 35 U.S.C. 154(b) by 156 days.

(21) Appl. No.: 13/848,280

(22) Filed: Mar. 21, 2013

(51) Int. Cl.
*G01N 33/00* (2006.01)
*B01J 8/00* (2006.01)
*B01J 19/00* (2006.01)
*B01J 35/00* (2006.01)
*B01J 35/02* (2006.01)

(52) U.S. Cl.
CPC ................................ *G01N 33/0009* (2013.01)

(58) Field of Classification Search
CPC .......... B01J 8/00; B01J 19/00; B01J 19/0006; B01J 19/0013; B01J 19/0093; B01J 35/00; B01J 35/02; B01J 2219/00279; B01J 2219/0068; B01J 2219/00702; B01J 2219/00704; B01J 2219/00781; B01J 2219/00788; B01J 2219/00792; B01J 2219/00873; G01N 33/00; G01N 33/0004; G01N 33/0009; G01N 33/0027; G01N 33/0031; G01N 33/0044; G01N 33/005

USPC ........ 422/129, 130, 600, 603, 650–655, 659
See application file for complete search history.

(56) References Cited

U.S. PATENT DOCUMENTS

| | | | |
|---|---|---|---|
| 3,665,240 A | | 5/1972 | Archer |
| 4,021,357 A | * | 5/1977 | Morduchowitz et al. .... 508/471 |
| 4,605,546 A | | 8/1986 | Voirin |
| 5,501,981 A | * | 3/1996 | Ray ...................... G01N 21/766 436/119 |
| 5,670,707 A | * | 9/1997 | Fennell ................. G01N 30/32 73/19.02 |
| 7,118,917 B2 | * | 10/2006 | Bergh et al. .................... 436/37 |
| 2002/0002794 A1 | | 1/2002 | Figueroa et al. |
| 2002/0182128 A1 | * | 12/2002 | Carnahan et al. ............. 422/188 |
| 2009/0317322 A1 | * | 12/2009 | Wolfert et al. ............... 423/564 |
| 2010/0280289 A1 | * | 11/2010 | De Winne et al. ........... 568/910 |
| 2012/0143515 A1 | | 6/2012 | Norman et al. |
| 2014/0322126 A1 | * | 10/2014 | Kubota et al. ................ 423/714 |

FOREIGN PATENT DOCUMENTS

WO        2010102653 A1      9/2010

* cited by examiner

*Primary Examiner* — Natasha Young
(74) *Attorney, Agent, or Firm* — Sherill Law Offices, PLLC

(57) ABSTRACT

A reactor capable of near absolute catalytic conversion of at least one alternative compound containing a specified moiety into a select compound containing the specific moiety, and an analytical instrument employing the reactor. The reactor including a catalytic element configured and arranged for fluid contact with a test fluid and a reactant, with at least 90% of the surface area of the catalytic element located within a thermal target zone in the reaction chamber of the reactor.

20 Claims, 3 Drawing Sheets

REACTOR FOR NEAR ABSOLUTE
CONVERSION OF ALTERNATIVE
MOIETY-CONTAINING SPECIES INTO A
SELECT MOIETY-CONTAINING SPECIES
AND ANALYTICAL INSTRUMENT
EMPLOYING THE REACTOR

BACKGROUND

It is often necessary, for consumer acceptance, improved shelf-life and/or regulatory compliance, to measure total content of a given moiety (e.g., sulfur) in a component or constituent employed in the production of a product and/or in the finished product, such as a processed comestible. Quantitative determination of total moiety content is typically achieved by catalytically converting all moiety-containing species in a sample into a single moiety-containing species and then measuring the concentration of that single species. For example, measurement of total sulfur content typically involves the conversion of various alternative sulfur-containing compounds potentially present in the sample gas (e.g., carbonyl sulfide (COS), methyl mercaptan ($CH_3SH$), ethyl mercaptan ($CH_4CH_3SH$), dimethyl sulfide ($CH_3SCH_3$), carbon disulfide ($CS_2$), 2-propanethiol ($CH_3SHC_2H_5$), tert-butyl mercaptan (($CH_3$)$_3CSH$), 1-propanethiol ($CH_3(CH_2)_2SH$), thiophene ($C_4H_4S$), n-butanethiol ($CH_3(CH_2)_3SH$), diethyl sulfide ($CH_3CH_2SCH_2CH_3$), methyl ethyl sulfide ($CH_3SCH_2CH_3$), 2-methyl-1-propanethiol (($CH_3$)$_2CHCH_2SH$), 1-methyl-1-propanethiol ($CH_3CH_2CHSHCH_3$), etc.) into hydrogen sulfide ($H_2S$) at approximately 1,000° C. in the presence of hydrogen and a nickel catalyst, followed by measurement of hydrogen sulfide in the converted sample with a suitable measuring instrument such as a gas chromatograph, mass spectrometer or photo-ionization detector.

This technique, while generally useful, lacks the accuracy, precision and sensitivity required for many applications, due in major part to vagaries resulting from and introduced by the required catalytic conversion of the single moiety-containing species into the select moiety-containing species.

Hence, a substantial need continues to exist for a highly sensitive analytical instrument capable of accurately and precisely measuring total moiety content (e.g., sulfur) in a test gas when one or more alternative moiety-containing species needs to be catalytically converted into a select moiety-containing species for measurement. More specifically, a substantial need continues to exist for a reactor capable of quickly achieving absolute catalytic conversion of alternative moiety-containing species into a single select moiety-containing species for subsequent measurement, in the absence of any appreciable absorption, adsorption or outgassing of the moiety or a moiety-containing compound.

SUMMARY OF THE INVENTION

A first aspect of the invention is a reactor for near absolute catalytic conversion of at least one alternative compound containing a specified moiety into a select compound containing the specific moiety. The reactor includes (a) a reaction chamber, (b) a tube defining a lumen configured and arranged for conveying a gaseous blend of a test fluid and a reactant along a path of travel bounded within the reaction chamber, (c) a heater operable for heating a target zone along the path of travel to within 10% of a target temperature, with a thermal gradient of greater than 20% occurring along the bounded path of travel, and (d) a catalytic element in fluid communication with the lumen, operable for catalyzing conversion of an alternative compound containing a specified moiety when in the presence of a reactant to a select compound containing the specific moiety at the target temperature, wherein at least 90% of the surface area of the catalytic element is located within the target zone.

A specific embodiment of the first aspect of the invention is a reactor for near absolute catalytic conversion of sulfur compounds to hydrogen sulfide.

A second aspect of the invention is an analytical instrument for measuring concentration of a moiety in a sample. The instrument includes (A) a reactor in accordance with the first aspect of the invention capable of converting a sample gas into a converted sample gas in which at least one alternative compound containing a specified moiety has been converted into a select compound containing the specific moiety, (B) a source of sample gas in fluid communication with a proximal end of the lumen, (C) a source of reactant gas in fluid communication with the proximal end of the lumen and operable for admixture with the sample gas prior to introduction of the sample gas into the reactor, and (D) a measuring instrument in fluid communication with a distal end of the lumen operable for detecting the select compound in a converted sample gas and establishing a quantitative value for total moiety content in the sample gas.

A specific embodiment of the second aspect of the invention is an instrument for measuring concentration of total sulfur in a sample by converting sulfur compounds to hydrogen sulfide and detecting the concentration of hydrogen sulfide in the converted sample.

DETAILED DESCRIPTION OF A PREFERRED
EMBODIMENT

Definitions

As used herein, including the claims, the phrase "near absolute" means at least 99.5%.

Figure 2:
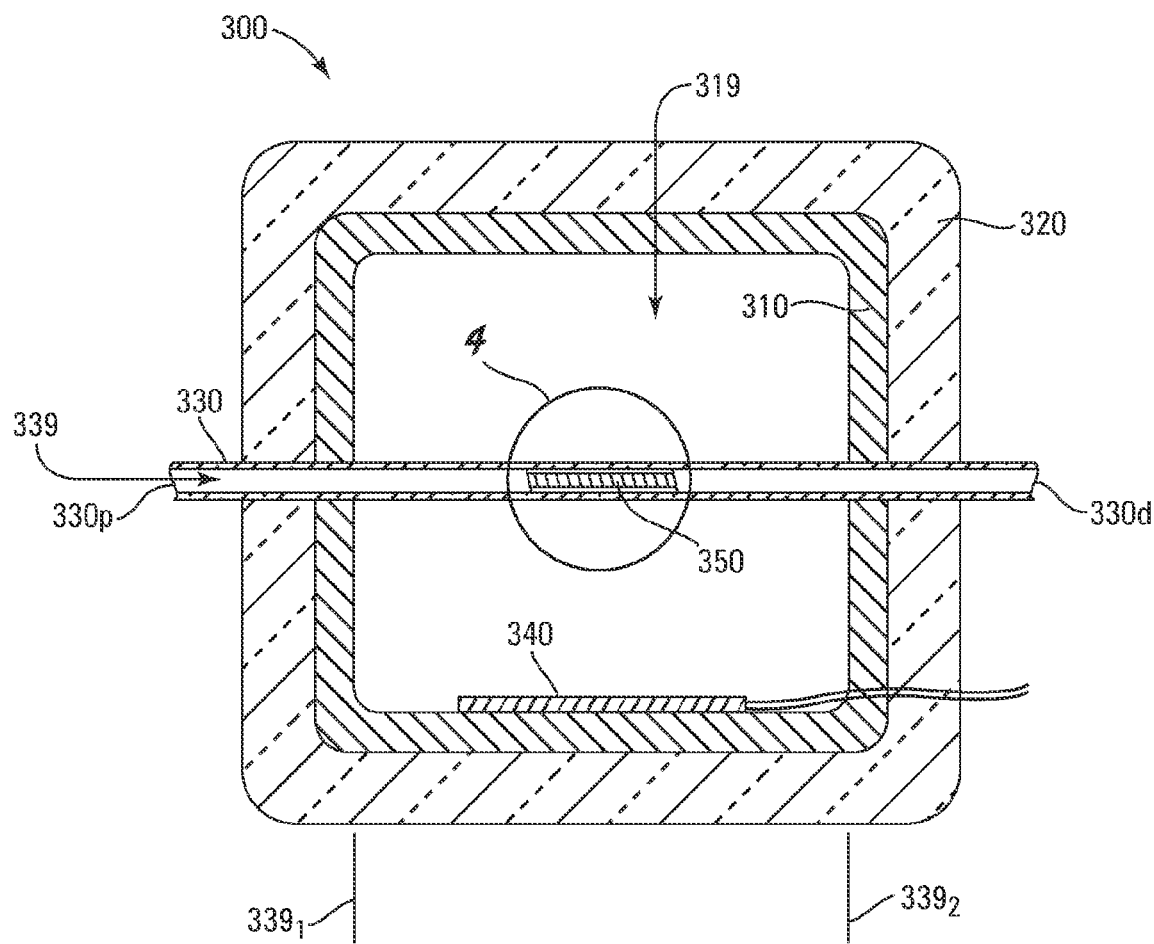
FIG. 2 is cross-sectional schematic diagram of one embodiment of the reactor aspect of the invention.

As used herein, including the claims, the phrase "path of travel" means the path along which a test fluid is constrained to travel within a reaction chamber bounded by the walls defining the reaction chamber. An exemplary linear path of travel 339 is depicted in FIG. 2 in which the path of travel is bounded by inlet boundary $339_1$ and outlet boundary $339_2$.

As used herein, including the claims, the phrase "target zone" ($T_{Zone}$) means that portion of a path of travel which is heated to or within an acceptable range of the target temperature.

As used herein, including the claims, the phrase "target temperature" ($T_{Target}$) means the temperature selected for attainment within a thermal controlled environment in order to achieve a desired effect, which for a catalytic reaction chamber is a temperature at which the desired catalytic reaction takes place with minimal side reaction.

NOMENCLATURE

100 Analytical Instrument
200 Source of Infeed Gases
210 Source of Sample or Test Gas
212 Valve for Source of Sample Gas
220 Source of Reactant Gas
222 Valve for Source of Reactant Gas
230 Mixing Chamber
300 Reactor
310 Reactor Vessel
319 Reaction Chamber
320 Insulation Surrounding Reaction Chamber
330 Tube
$330_d$ Distal End of Tube
$330_p$ Proximal End of Tube
332 Retention Crimps in Tube
339 Lumen of Tube (Path of Travel)
$339_1$ Inlet Boundary of Path of Travel
$339_2$ Outlet Boundary of Path of Travel
340 Heater
350 Catalytic Element
359 Bore of Catalytic Element
400 Measuring Instrument
402 Sampling Valve
500 Electronic Controller
600 Component Interconnecting Tubing
$600_1$ Tubing Connecting Source of Sample or Test Gas to Mixing Chamber
$600_2$ Tubing Connecting Source of Reactant to Mixing Chamber
$600_3$ Tubing Connecting Mixing Chamber to Inlet of Reactor
$600_4$ Tubing Connecting Outlet of Reactor to Sampling Valve
$600_5$ Tubing Venting Sampling Valve to Atmosphere
$600_6$ Tubing Connecting Sampling Valve to Measuring Instrument
700 Thermal Gradient
$T_{Target}$ Target Temperature
$T_{Zone}$ Target Zone

Construction

Referring to FIG. 2, a first aspect of the invention is a reactor 300 for near absolute catalytic conversion of at least one alternative compound containing a specified moiety into a select compound containing a specific moiety. The reactor 300 is particularly suited for catalytic conversion of various alternative sulfur-containing compounds, such as mercaptans, into hydrogen sulfide ($H_2S$). Hence, for purposes of providing a clear and lucid disclosure of the invention without intending to be limited thereby, the balance of the disclosure may periodically reference sulfur (S) as the specified moiety, mercaptans (RSH) as the alternative compounds, hydrogen as the added reactant, and hydrogen sulfide ($H_2S$) as the select compound.

The reactor 300 includes a reactor vessel 310 defining a reaction chamber 319, a tube 330 defining a lumen 339, a heater 340 and a catalytic element 350.

The reactor vessel 310 is preferably surrounded by thermal insulation 320 and must be constructed from a material capable of withstanding the temperatures at which the catalytic conversion of alternative compounds to the select compound takes place, which for the conversion of mercaptans to hydrogen sulfide employing a nickel catalyst is 1000° C.±100° C. The reactor vessel 310 and thermal insulation 320 are preferably constructed as a single unitary component from a refractory ceramic material.

The reactor vessel 310 may have any desired size and shape. When intended for use as a reactor vessel 310 in an analytical instrument 100 for measuring concentration of a moiety in a sample, the reactor vessel 310 needs to be large enough to provide a reaction chamber 319 capable of achieving near absolute conversion of alternative compounds to the select compound in a sample flowing through the reaction chamber 319, but small enough to rest upon a workbench with a preference for a portable unit. Generally, a reactor vessel 310 defining a reaction chamber 319 of between 6 $cm^3$ to 20 $cm^3$ achieves the desired balancing of these competing variables.

The tube 330 extends through the reaction chamber 319 for conveying a gaseous blend of a test fluid and a reactant within the lumen 339 of the tube 330 along a path of travel 339 bounded by the walls of the reaction vessel 310 defining the reaction chamber 319. The proximal $330_p$ and distal $330_d$ ends of the tube 330 extend outward from the reactor vessel 310 and the surrounding insulation 320 for sealed coupling to feed streams 200 of test fluid and added reactant at the proximal end $330_p$ and sealed coupling to a measuring instrument 400 at the distal end $330_d$.

Since the tube 330 will be in physical contact with the test fluid before, during and after catalytic conversion of alternative compounds in the test fluid into the select compound, the tube 330 is constructed from a material capable of not only withstanding the temperatures at which the catalytic conversion of alternative compounds to the select compound takes place, but must also be inert with respect to the alternative compounds, added reactant and select compound, and must not appreciably absorb, adsorb or outgas the alternative compounds, added reactant and/or select compound. When used to convert sulfur-containing alternative compounds into hydrogen sulfide ($H_2S$) using hydrogen reactant and a nickel catalyst, the preferred material of construction is quartz.

When the reactor 300 is intended for use in an analytical instrument 100 for measuring concentration of a moiety in a sample, the lumen 339 of the tube 330 preferably has a diameter of about 3 mm to 1 mm and provides a path of travel 339 between about 4 and 15 cm long. A lumen 339 with a diameter smaller than about 1 mm results in unnecessary delays in testing resulting from reduced flow rates through the lumen 339, while a lumen 339 with a diameter larger than about 3 mm increases the size and cost of the reactor 300 without any concomitant benefit, and increases the likelihood that test fluid can pass through the lumen 339 without contacting the catalytic element 350 and thereby pass through the reactor 300 unconverted. A path of travel 339 smaller than about 4 mm tends to result in an incomplete conversion of alternative compounds into the select compound, while a path of travel 339 larger than about 15 mm increases the size and cost of the reactor 300 without any concomitant benefit. The preferred length for the path of travel 339 is between 6 and 10 cm.

The heater 340 heats the reaction chamber 319, and thereby the catalytic element 350 and fluids flowing through the lumen 339 of the tube 330, to a target temperature $T_{Target}$ at which the desired catalytic conversion takes place, which for the conversion of mercaptans to hydrogen sulfide employing a nickel catalyst is 1000° C.±100° C. The heater 340 is preferably embedded within the walls of a unitarily formed reactor vessel 310 and thermal insulation 320. An exemplary suitable heater 340 is a ceramic fiber heater Model VC400-L02JB available from Watlow Electric Manufacturing Company of St. Louis, Mo., USA.

Figure 3:
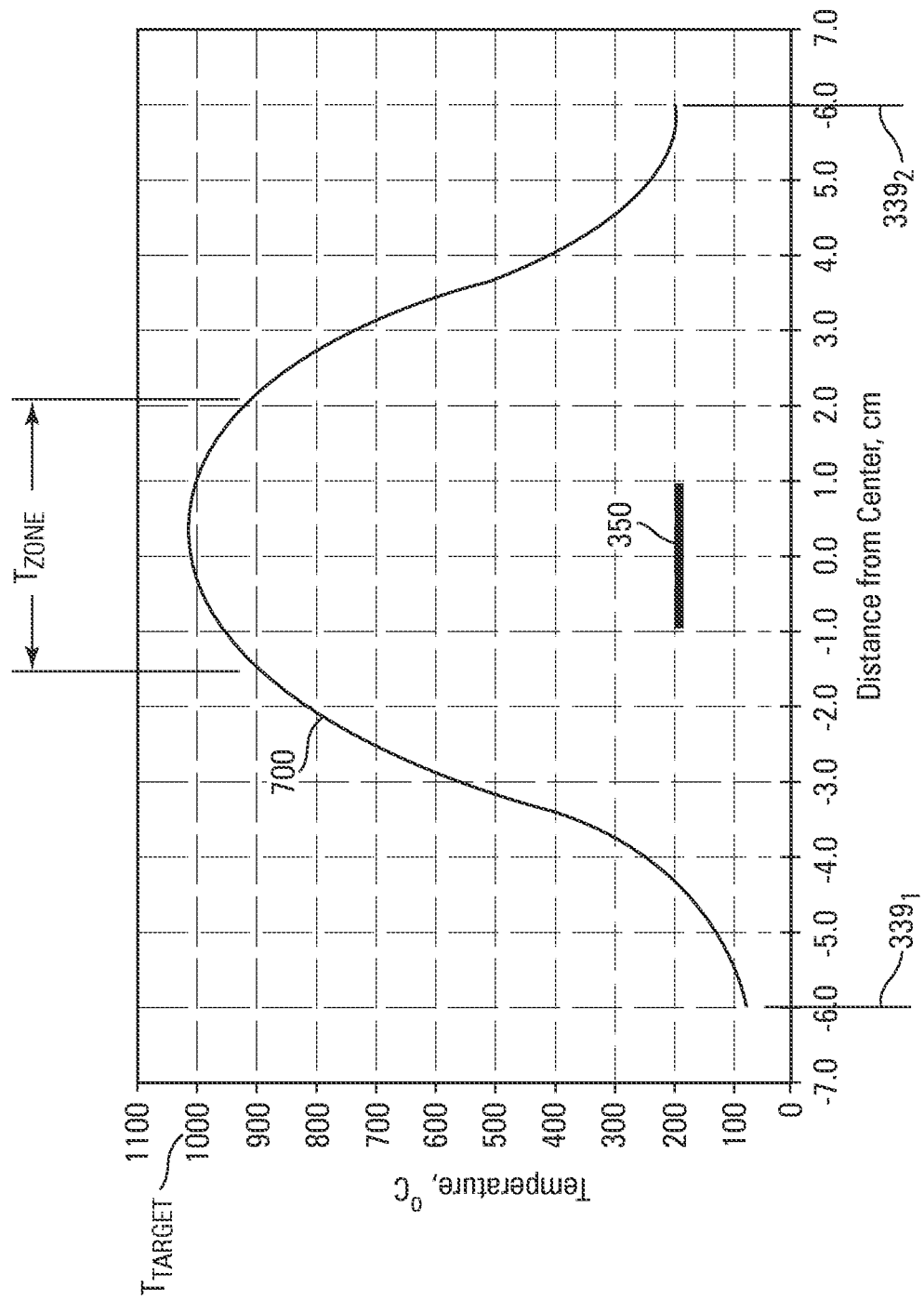
FIG. 3 is a graphical representation of an exemplary thermal gradient along the path of travel depicted in FIG. 2 including a depiction of the catalytic element relative to the thermal gradient.

Referring to FIG. 3, despite all efforts to provide a uniform temperature profile throughout the reaction chamber 319 and along the entire path of travel 339 defined by the lumen 339 of the tube 330, a thermal gradient 700 (e.g., 20% change) invariably exists along the path of travel 339 in such reaction chambers 319. Only a portion of the path of travel 339, referenced as a target zone $T_{Zone}$, is heated to or within an acceptable range (e.g., 10%, preferably 5%, most preferably 3%) of the target temperature $T_{Target}$ at which the desired catalytic conversion takes place, while the balance of the path of travel 339 is heated to a temperature which falls below the accepted range. This thermal gradient 700 can range from less than about 10% to as much as 80% depending upon a wide range of variables, which for a target temperature $T_{Target}$ of 1000° C. such as employed when converting mercaptans to hydrogen sulfide using a nickel catalyst, is a range of from less than 100° C. to as much as 800° C.

The catalytic element 350 needs to be in fluid communication with the lumen 339 of the tube 330 where it can contact and catalyze conversion of alternative compounds in the test fluid to the select compound. The catalytic element 350 also needs to have a predominant portion of its surface area located within the target zone $T_{Zone}$ to reduce the conversion of alternative compounds in the test fluid to compounds other than the select compound. The catalytic element 350 is preferably positioned and arranged so that at least 90%, most preferably at least 98% and ideally 100%, of the surface area of the catalytic element is located within the target zone $T_{Zone}$.

Figure 4:
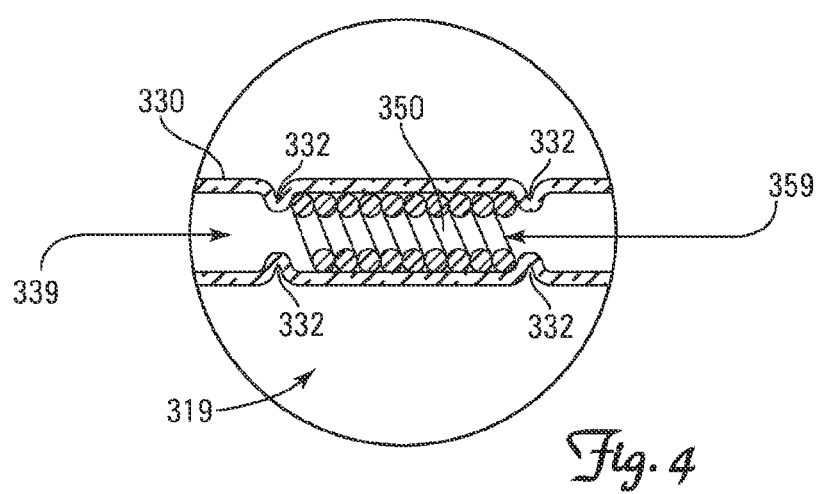
FIG. 4 is a grossly-enlarged cross-sectional side view of the target zone of the reactor depicted in FIG. 2.

Referring to FIG. 4, a preferred shape for the catalytic element 350 is a helix having an outer diameter just slightly smaller than the diameter of the lumen 339 for ease of insertion and positioning with the lumen 339, and providing a bore 359 of reduced diameter relative to the lumen 339 so that when the bore 359 is positioned concentrically within the lumen 339 the test fluid and added reactant will flow under nonlaminar conditions so as to minimize the possibility that alternative compounds in the test fluid can flow past the catalytic element 350 without contacting the catalytic element 350 and escape conversion to the select compound. The catalytic element 350 preferably has a length of about 0.5 to 3 cm, with a length of less than 0.5 cm susceptible to incomplete conversion of alternative compounds to the select compound, while a length of greater than about 3 cm increases the size and cost of the reactor 300 without any concomitant benefit. The helical catalytic element 350 can be restrained at the desired location within the lumen 339 and within the target zone $T_{Zone}$ by forming crimps 332 in the tube 330 proximate either end of the catalytic element 350 which extend a sufficient distance into the lumen 339 to prevent the catalytic element 350 from sliding past the crimps 332 without adversely reducing fluid flow through the lumen 339 and the bore 359 of the catalytic element 350.

Figure 1:
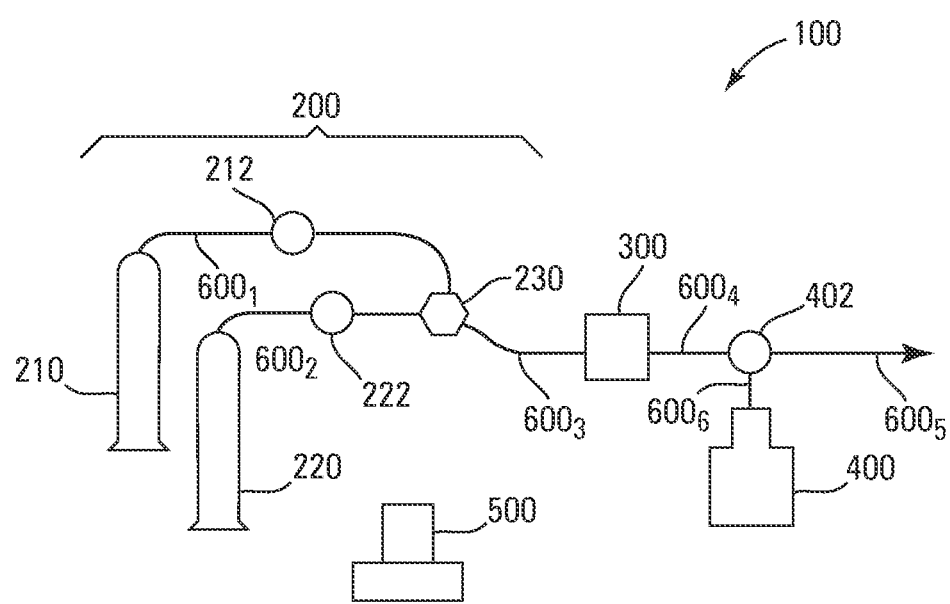
FIG. 1 is a schematic diagram of one embodiment of the analytical instrument aspect of the invention.

Referring to FIG. 1, a second aspect of the invention is an analytical instrument 100 for measuring concentration of a moiety in a sample that employs the reactor 300 of the first aspect of the invention. The analytical instrument 100 is particularly suited for measuring total sulfur in a test sample by catalytically converting the various alternative sulfur-containing compounds, such as mercaptans, into hydrogen sulfide ($H_2S$) and then measuring the concentration of hydrogen sulfide ($H_2S$) in the converted sample. Hence, for purposes of providing a clear and lucid disclosure of the invention without intending to be limited thereby, the balance of the disclosure may periodically reference sulfur (S) as the specified moiety, mercaptans (RSH) as the alternative compounds, hydrogen as the added reactant, and hydrogen sulfide ($H_2S$) as the select compound.

The instrument 100 includes a reactor 300 in accordance with the first aspect of the invention, a source of test gas 210, optionally a source of reactant gas 220, and a measuring instrument 400. Operation of the entire instrument 100 is preferably controlled by a suitable electronic controller 500.

The reactor 300 is capable of converting a sample gas into a converted sample gas in which at least one alternative compound (e.g., mercaptans) containing a specified moiety (e.g., sulfur) has been converted into a select compound (e.g., hydrogen sulfide) for subsequent detecting and quantification by the measuring instrument 400.

The inlet $330_p$ into the reactor 300 is in sealed fluid communication with a source of test gas 210 and, when needed to effect the desired catalytic reaction, a source of one or more reactant gases 220. The gases are preferably blended together into a homogenous feedstock in a mixing chamber 230 prior to introduction into the reactor 300. Flow control valves 212 and 222 are provided in the tubing $600_1$ and $600_2$ connecting the source of test gas 210 and source of reactant gas 220 respectively, for purposes of allowing desired stoichiometric addition of the test gas and reactant gas. The blended feedstock is then delivered to the inlet of the reactor 300 via tubing $600_3$.

Catalytically converted test fluid exiting the reactor 300 is directed by tubing $600_4$ to a sampling valve 402 for selective delivery of the catalytically converted test fluid to atmosphere through tubing $600_5$ or to a measuring instrument 400 via tubing $600_6$ for detection and measurement of the select compound containing the specific moiety, from which the total concentration of the specific moiety in the original test fluid can be ascertained.

The measuring instrument 400 may be selected from any of the well known analyte detection and measurement instruments. Selection of the measuring instrument 400 depends upon a variety of variables including the select compound or analyte to be measured, the sensitivity desired and cost. Widely employed measuring instruments 400 include specifically but not exclusively, gas chromatographs, mass spectrometers, photo-ionization detectors, photoluminescent detectors, chemiluminescent detectors, colorimetric gas detection tubes, flame ionization detectors, thermal conductivity detectors, and the like.

The analytical instrument 100 is controlled by a suitable electronic control device 500 which may be provided as an onboard microcontroller or CPU, or as a separate CPU in communication with the various components of the analytical instrument 100 involved in proportion and flow rate control of the feedstock, operation of the heater 340 including selection of the target temperature $T_{Target}$ and operation of the measuring instruments 400. Suitable user interface devices (not depicted) are also provided, including display, keyboard, mouse, touch screen, etc.

We claim:

1. An analytical instrument for measuring concentration of sulfur in a sample, the instrument comprising:
(a) a reactor including at least (i) a reaction chamber, (ii) a single tube defining a lumen configured and arranged for conveying a gaseous blend of a test fluid and hydrogen along a path of travel bounded within the reaction chamber, (iii) a heater operable for heating a target zone along the path of travel to within 10% of a target temperature, with a thermal gradient of greater than 20% occurring along the bounded path of travel, and (iv) a catalytic element in fluid communication with the lumen, operable for catalyzing conversion of an alternative compound containing sulfur when in the presence of hydrogen to hydrogen sulfide at the target temperature, wherein at least 90% of the surface area of the catalytic element is located within the target zone, (v) wherein the reactor is capable of converting a sample gas into a converted sample gas in which at least one alternative compound containing sulfur has been converted into hydrogen sulfide, (b) a source of sample gas of indeterminate composition in fluid communication with a proximal end of the lumen, (c) a source of hydrogen gas in fluid communication with the proximal end of the lumen and operable for admixture with the sample gas prior to introduction of the sample gas into the reactor, and (d) a measuring instrument in fluid communication with a distal end of the lumen responsive to hydrogen sulfide and thereby operable for establishing a quantitative value for total sulfur content in the sample gas upon catalytic conversion of alternative compounds containing sulfur into hydrogen sulfide.

2. The analytical instrument of claim 1 wherein the measuring instrument is a photo-ionization detector.

3. The analytical instrument of claim 1 wherein the lumen has a diameter of about 1 to 3 mm.

4. The analytical instrument of claim 1 wherein the lumen has a diameter of about 1 to 2 mm.

5. The analytical instrument of claim 1 wherein the bounded path of travel is between about 4 to 15 cm long.

6. The analytical instrument of claim 5 wherein the tube is a hollow quartz tube.

7. The analytical instrument of claim 1 wherein the bounded path of travel is linear and between 6 to 10 cm long.

8. The analytical instrument of claim 1 wherein the target zone is that zone heated to within 5% of the target temperature.

9. The analytical instrument of claim 1 wherein the target zone is that zone heated to within 3% of the target temperature.

10. The analytical instrument of claim 9 wherein the thermal gradient along the bounded path of travel is greater than 50%.

11. The analytical instrument of claim 10 wherein the thermal gradient along the bounded path of travel is greater than 500° C.

12. The analytical instrument of claim 11 wherein the catalytic element extends about 0.5 to 1.5 cm along the path of travel.

13. The analytical instrument of claim 9 wherein the thermal gradient along the bounded path of travel is greater than 200° C.

14. The analytical instrument of claim 1 wherein the thermal gradient along the bounded path of travel is greater than 30%.

15. The analytical instrument of claim 1 wherein the thermal gradient along the bounded path of travel is greater than 100° C.

16. The analytical instrument of claim 1 wherein 98% of the surface area of the catalytic element is within the target zone.

17. The analytical instrument of claim 1 wherein the entire catalytic element is within the target zone.

18. The analytical instrument of claim 1 wherein the catalytic element extends between about 0.5 to 2 cm along the path of travel.

19. The analytical instrument of claim 1 wherein the catalytic element is a coil with a bore concentrically positioned within the lumen.

20. The analytical instrument of claim 1 wherein the catalytic element is nickel and the target temperature is 1000° C.±100° C.

* * * * *